US011672692B2

(12) United States Patent
Yoda et al.

(10) Patent No.: US 11,672,692 B2
(45) Date of Patent: Jun. 13, 2023

(54) HEATING DEVICE (71) Applicant: TOYOTA BOSHOKU KABUSHIKI KAISHA, Aichi-ken (JP)

(72) Inventors: Takumi Yoda, Aichi-ken (JP); Fumitoshi Akaike, Aichi-ken (JP); Kohei Nakamura, Aichi-ken (JP)

(73) Assignee: TOYOTA BOSHOKU KABUSHIKI KAISHA, Aichi-ken (JP)

( * ) Notice: Subject to any disclaimer, the term of this patent is extended or adjusted under 35 U.S.C. 154(b) by 656 days.

(21) Appl. No.: 16/821,138

(22) Filed: Mar. 17, 2020

(65) Prior Publication Data
US 2020/0297965 A1 Sep. 24, 2020

(30) Foreign Application Priority Data

Mar. 20, 2019 (JP) .............................. JP2019-052401

(51) Int. Cl.
*A61M 21/00* (2006.01)
*H05B 6/06* (2006.01)
(Continued)

(52) U.S. Cl.
CPC ................ *A61F 7/00* (2013.01); *A61M 21/00* (2013.01); *H05B 6/06* (2013.01);
(Continued)

(58) Field of Classification Search
CPC ...... A61F 2007/0024; A61F 2007/0041; A61F 2007/0043; A61F 2007/0052;
(Continued)

(56) References Cited

U.S. PATENT DOCUMENTS 4,677,281 A 6/1987 Mills
2010/0117410 A1 5/2010 Akaike et al.
(Continued)

FOREIGN PATENT DOCUMENTS

CN 101687470 3/2010
CN 106133450 11/2016
(Continued)

OTHER PUBLICATIONS

Official Action in JP application No. 2019-052401 dated Jul. 20, 2022, along with English-language translation thereof.
(Continued)

*Primary Examiner* — Tigist S Demie
(74) *Attorney, Agent, or Firm* — Greenblum & Bernstein, P.L.C.

(57) ABSTRACT

A heating device includes:
  a temperature change unit that changes a temperature of a temperature change area;
  an induction unit that applies a stimulus to an induction area; and
  a controller,
  wherein the induction area is an area on skin surface, or an area that occupies a space that can be perspectively projected on the skin surface,
  the induction area is an area that does not overlap with the temperature change area,
  the induction unit applies at least one of a tactile stimulus and a visual stimulus to the induction area,
  the controller executes a first control for changing a temperature of a first temperature change area of the temperature change area and a second control for applying a stimulus to a first induction area of the induction area, and
(Continued)

the second control is performed in accordance with the first control.

12 Claims, 6 Drawing Sheets

(51) Int. Cl.
*A61F 7/00* (2006.01)
*A61F 7/02* (2006.01)

(52) U.S. Cl.
CPC .......... *A61F 2007/0052* (2013.01); *A61F 2007/0086* (2013.01); *A61F 2007/0093* (2013.01); *A61F 2007/0295* (2013.01); *A61M 2021/0022* (2013.01); *A61M 2021/0044* (2013.01); *A61M 2021/0066* (2013.01); *A61M 2210/04* (2013.01)

(58) Field of Classification Search
CPC ...... A61F 2007/0071; A61F 2007/0086; A61F 2007/0093; A61F 2007/0295; A61F 7/00; A61F 7/0053; A61F 7/007; H05B 6/06
See application file for complete search history.

(56) References Cited

U.S. PATENT DOCUMENTS

| | | | |
|---|---|---|---|
| 2014/0303694 A1* | 10/2014 | Timme | A61M 16/0003 607/96 |
| 2017/0144574 A1 | 5/2017 | Tanaka et al. | |
| 2017/0156923 A1 | 6/2017 | Utturkar et al. | |
| 2018/0000352 A1 | 1/2018 | Starr et al. | |

FOREIGN PATENT DOCUMENTS

| | | |
|---|---|---|
| CN | 206102147 | 4/2017 |
| CN | 107714007 | 2/2018 |
| CN | 108478926 | 9/2018 |
| JP | 2001-112565 | 4/2001 |
| JP | 2003-65613 | 3/2003 |
| JP | 2003-308009 | 10/2003 |
| JP | 6360636 | 7/2018 |

OTHER PUBLICATIONS

Chinese Office Action in Chinese Application No. 202010195878.0 dated Feb. 14, 2022, along with English-language translation.
Keegan et al., "The Segmental Distribution of the Cutaneous Nerves in the Limbs of Man", 1948, pp. 409-437.

* cited by examiner

HEATING DEVICE

TECHNICAL FIELD

The present disclosure relates to a heating device.

BACKGROUND ART

An air conditioner or a heater is used as a heating appliance indoors or in an automobile. The heating appliance increases a temperature of air indoors or in the automobile by heating the air indoors or in the automobile. Therefore, a person who is indoor or in the automobile can work in a warm environment having a higher temperature.

On the other hand, a visual heating effect has also been researched and developed. For example, JP-A-2003-65613 discloses a technique of arranging a light source in the vicinity of a radiation body separately from a radiation body that does not generate light (paragraph [0006] of JP-A-2003-65613).

Further, it is disclosed that brightness of a LED is changed in accordance with estimated temperature of the radiation body (paragraph [0029] of JP-A-2003-65613). Accordingly, it is described that a person can obtain a visual heating effect and that a person can easily understand that the radiation body has a high temperature (paragraph [0007] of).

Immediately after start of an operation of the heating appliance, a temperature of a human skin surface is not so high as to cause a warm feeling. In the technique described in JP-A-2003-65613, in a case where the estimated temperature of the radiation body is so low that the temperature of the skin surface cannot be changed to a temperature greater than or equal to a warm feeling threshold, the heating appliance cannot make the person feel warmth. In addition, the same applies to ordinary heating appliances other than JP-A-2003-65613.

Therefore, for example, it is preferable that the heating appliance makes the person feel warmth even immediately after the start of the heating. For this purpose, it is desirable to make the person feel higher skin surface temperature higher than actual skin surface temperature. As a result, the person can feel warmth with a small heat output. In this case, an energy-saving effect is obtained.

A problem to be solved by the present disclosure is to provide a heating device that can give a person a local warmer feeling even if the temperature of the skin surface does not exceed the warm feeling threshold.

SUMMARY

According to an aspect of the disclosure, A heating device includes:

a temperature change unit that is configured to change a temperature of a temperature change area on a human or animal skin surface;

an induction unit that is configured to apply a stimulus to an induction area; and a controller, wherein the induction area is an area on the human or animal skin surface, or an area that occupies a space that can be perspectively projected on the human or animal skin surface from a viewpoint of a person or an animal, the induction area is an area that does not overlap with the temperature change area, the induction unit is configured to apply at least one of a tactile stimulus and a visual stimulus to the induction area, the controller is configured to execute a first control for changing a temperature of at least a part of a first temperature change area of the temperature change area and a second control for applying a stimulus to at least a part of a first induction area of the induction area, and the second control is performed in accordance with the first control.

The heating device can give a person a local warmer feeling regardless of actual skin surface temperature. Therefore, it is possible to make the person feel warmth at an early stage even at start of heating. In addition, the person can feel warmth with a small heat output. That is, the heating device has an energy-saving effect.

In the present disclosure, there is provided a heating device that can give a person a local warmer feeling.

DESCRIPTION OF EMBODIMENTS

Hereinafter, specific embodiments will be described by taking a heating device as an example. However, the present disclosure is not limited to these embodiments.

First Embodiment

1. Heating Device

Figure 1:
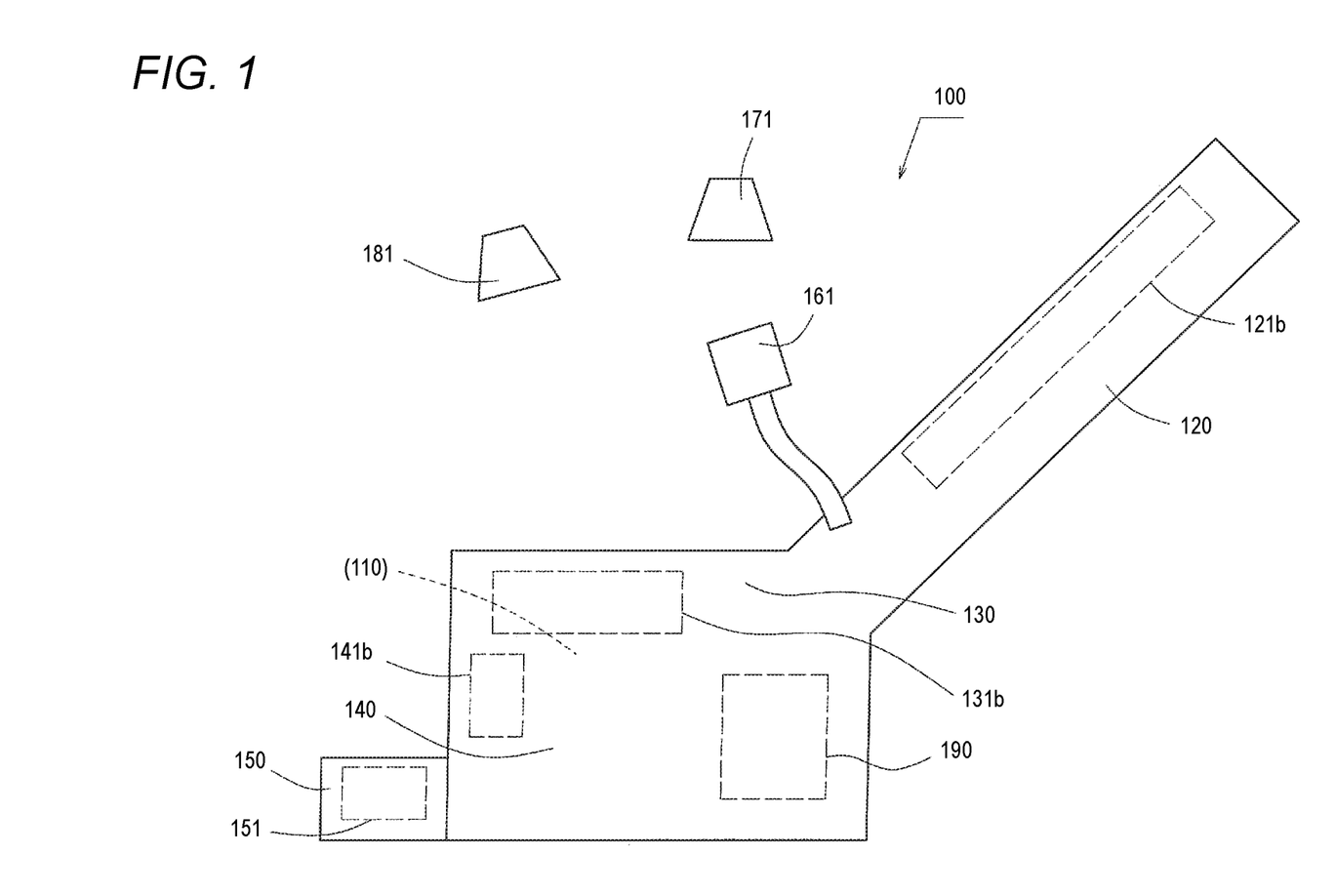
FIG. 1 is a side view showing a schematic configuration of a heating device according to a first embodiment.
Figure 2:
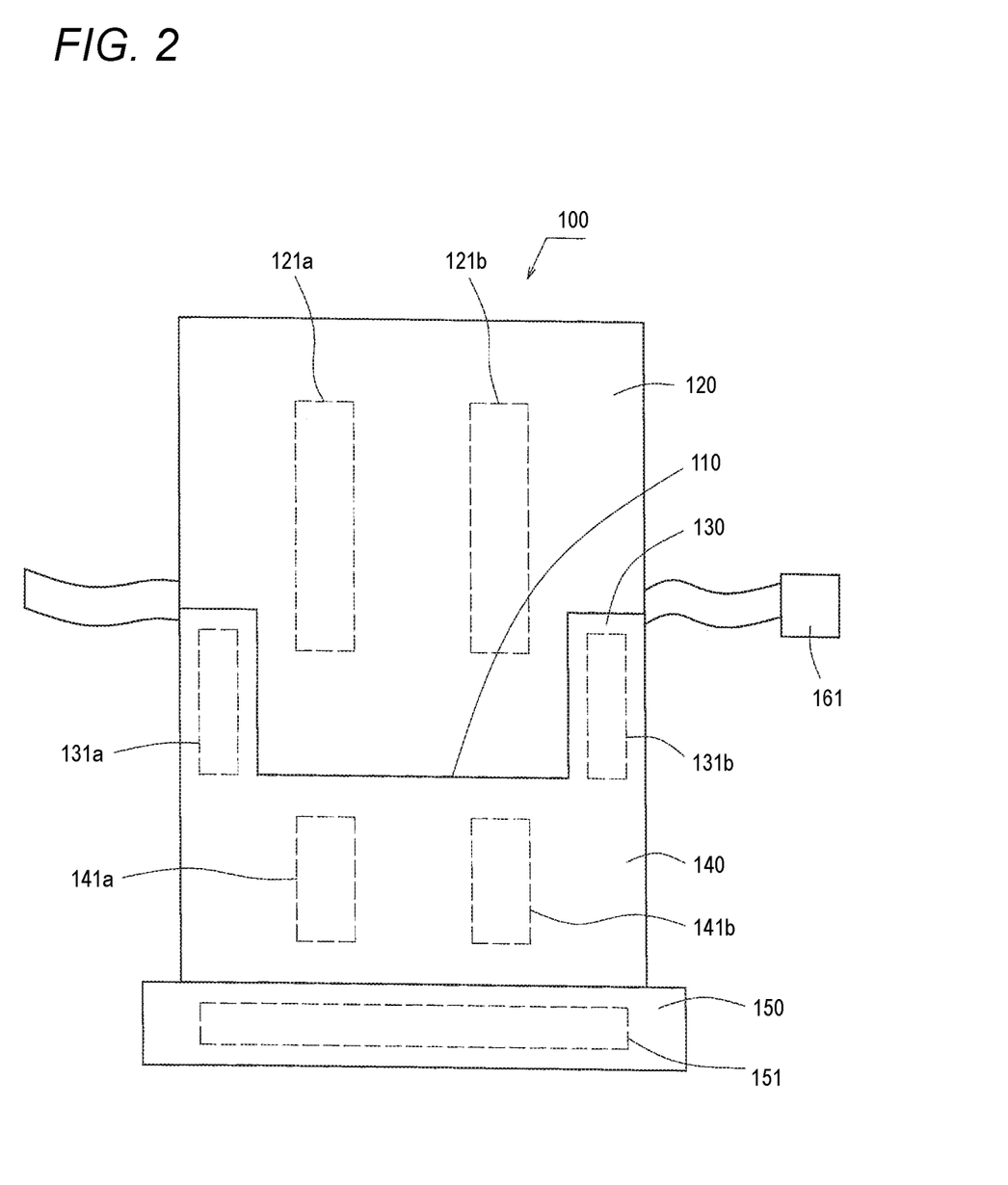
FIG. 2 is a front view showing the schematic configuration of the heating device according to the first embodiment.

FIG. 1 is a side view showing a schematic configuration of a heating device 100 according to a first embodiment. FIG. 2 is a front view showing the schematic configuration of the heating device 100 according to the first embodiment. As shown in FIGS. 1 and 2, the heating device 100 is a chair-type device. Therefore, a person can sit on the heating device 100.

The heating device 100 includes a seat portion 110, a back portion 120, a side portion 130, a leg portion 140, and a foot portion 150. The seat portion 110 is a member for the person to sit on. The back portion 120 is a member on which the person can lean. The side portion 130 is a member positioned outside a thigh portion of the person when the person is sitting on the seat portion 110. The leg portion 140 is a member positioned on a back side of a calf of the person when the person is sitting on the seat portion 110. The foot portion 150 is a member positioned on a foot sole side of the person when the person is sitting on seat portion 110.

In addition to the above, the heating device 100 includes back heating units 121a, 121b, thigh side heating units 131a, 131b, calf heating units 141a, 141b, a foot sole vibration unit 151, an abdomen vibration unit 161, an abdomen irradiation unit 171, a thigh irradiation unit 181, and a controller 190.

The back heating units 121a, 121b, the thigh side heating units 131a, 131b, and the calf heating units 141a, 141b are temperature change units for change temperatures of temperature change areas of a human skin surface, as will be described later. The temperature change unit changes the temperature of the temperature change area. Pressure variation in a contact range before and after the temperature change in the temperature change area is preferably less than a discrimination threshold of the person.

The foot sole vibration unit 151, the abdomen vibration unit 161, the abdomen irradiation unit 171, and the thigh irradiation unit 181 are induction units for applying a stimulus to induction areas of the human skin surface, as will be described later. The induction unit can make the person feel a local temperature of the induction area equal to or higher than an actual local skin temperature.

The back heating unit 121a heats a right back portion of the person. The back heating unit 121b heats a left back portion of the person. The left and right back portions of the person are the temperature change areas. The back heating units 121a, 121b are, for example, infrared ray irradiation units that irradiate the back of the person with infrared rays. The back heating units 121a, 121b may also be heaters.

The thigh side heating unit 131a heats an outer side surface of a right thigh portion of the person. The thigh side heating unit 131b heats an outer side surface of a left thigh portion of the person. The right and left thigh side portions of the person are the temperature change areas. The thigh side heating units 131a, 131b are, for example, infrared ray irradiation units that irradiate the thigh side portions of the person with the infrared rays. The thigh side heating units 131a, 131b may also be heaters.

The calf heating unit 141a heats a right calf of the person. The calf heating unit 141b heats a left calf of the person. The left and right calves of the person are the temperature change areas. The calf heating units 141a, 141b are, for example, infrared ray irradiation units that irradiate the calves of the person with the infrared rays. The calf heating units 141a, 141b may also be heaters.

The foot sole vibration unit 151 applies vibration to soles of both feet of the person. The soles of the both feet of the person are the induction areas. A vibration frequency is, for example, 1 Hz or more and 1000 Hz or less. Other numerical values may be used.

The abdomen vibration unit 161 applies vibration to an abdomen of the person. Therefore, the abdomen vibration unit 161 has a belt-shape portion, and the abdomen vibration unit 161 can contact the abdomen of the person. The abdomen of the person is the induction area. A vibration frequency is, for example, 1 Hz or more and 1000 Hz or less. Other numerical values may be used.

The abdomen irradiation unit 171 irradiates the abdomen of the person with a visual stimulus. Further, the abdomen irradiation unit 171 irradiates a position where the person can visually recognize the visual stimulus applied to the abdomen with the visual stimulus. The abdomen of the person is the induction area. The abdomen irradiation unit 171 hardly applies heat to the abdomen of the person.

The thigh irradiation unit 181 irradiates a front portion of the thigh portion of the person with the visual stimulus. The front portion of the thigh portion of the person is the induction area.

The controller 190 controls each unit as will be described later.

2. Control System of Heating Device 2-1. Control System

Figure 3:
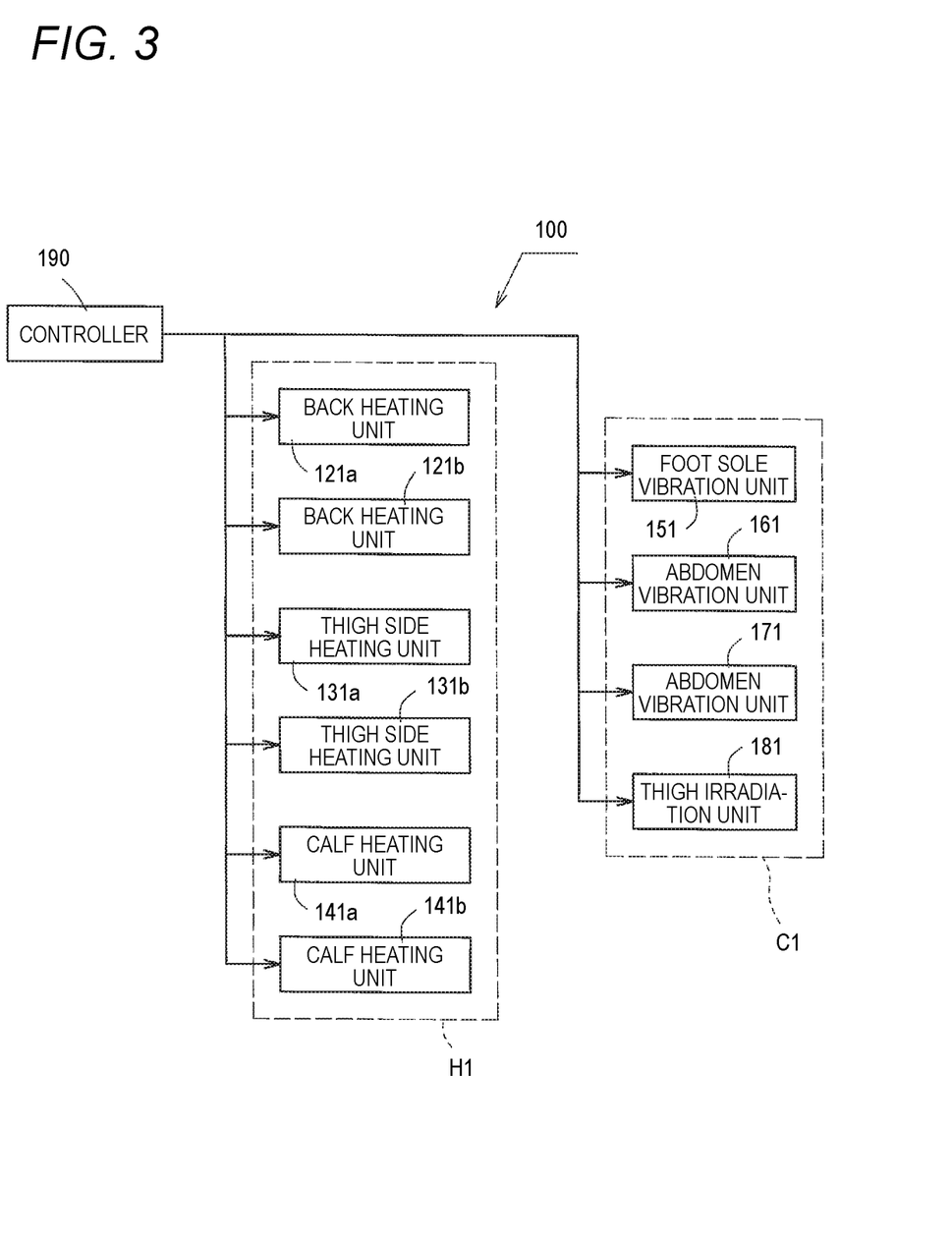
FIG. 3 is a block diagram showing a control system of the heating device according to the first embodiment.

FIG. 3 is a block diagram showing a control system of the heating device 100 according to the first embodiment. As shown in FIG. 3, the controller 190 controls a temperature change unit H1 and an induction unit C1. The temperature change unit H1 is used for change the temperature of the temperature change area of the human skin surface. The induction unit C is used for applying a stimulus to the induction area of the human skin surface. The induction unit C1 can apply at least one of a tactile stimulus and the visual stimulus to the induction area. Here, the temperature change area is an area that does not overlap with the induction area.

The temperature change unit H1 includes the back heating units 121a, 121b, the thigh side heating units 131a, 131b, and the calf heating units 141a, 141b. As will be described later, the temperature change unit H1 heats the temperature change area while alternately repeating a heating period during which the temperature change area is heated and a non-heating period during which the temperature change area is not heated.

The induction unit C1 includes the foot sole vibration unit 151, the abdomen vibration unit 161, the abdomen irradiation unit 171, and the thigh irradiation unit 181. The induction unit C1 includes a light irradiation unit that irradiates the induction area with the visual stimulus, and a vibration unit that applies vibration to the induction area. The light irradiation unit applies the visual stimulus, such as light, to the person. The light irradiation unit irradiates the human skin surface or a surface of clothes with light. The vibration unit applies the tactile stimulus, such as the vibration, to the person.

In this way, the controller 190 controls the back heating units 121a, 121b, the thigh side heating units 131a, 131b, the calf heating units 141a, 141b, the foot sole vibration unit 151, the abdomen vibration unit 161, the abdomen irradiation unit 171, and the thigh irradiation unit 181.

2-2. First Control and Second Control

The controller 190 can execute a first control for changing the temperature of the temperature change area and a second control for applying the stimulus to the induction area. The second control is performed in accordance with the first control. The first control is a first temperature change control. The second control is a first induction control.

A start timing of the second control is a timing after a start timing of the first control and before an end timing of the first control.

Here, the phrase "in accordance with" means that the second control follows the first control. It does not mean that the first control and the second control are executed at the same timing. That is, it means that the second control is started while the first control is in an ON state.

3. Stimulus (Operation) Applied to Person by Heating Device

Figure 4:
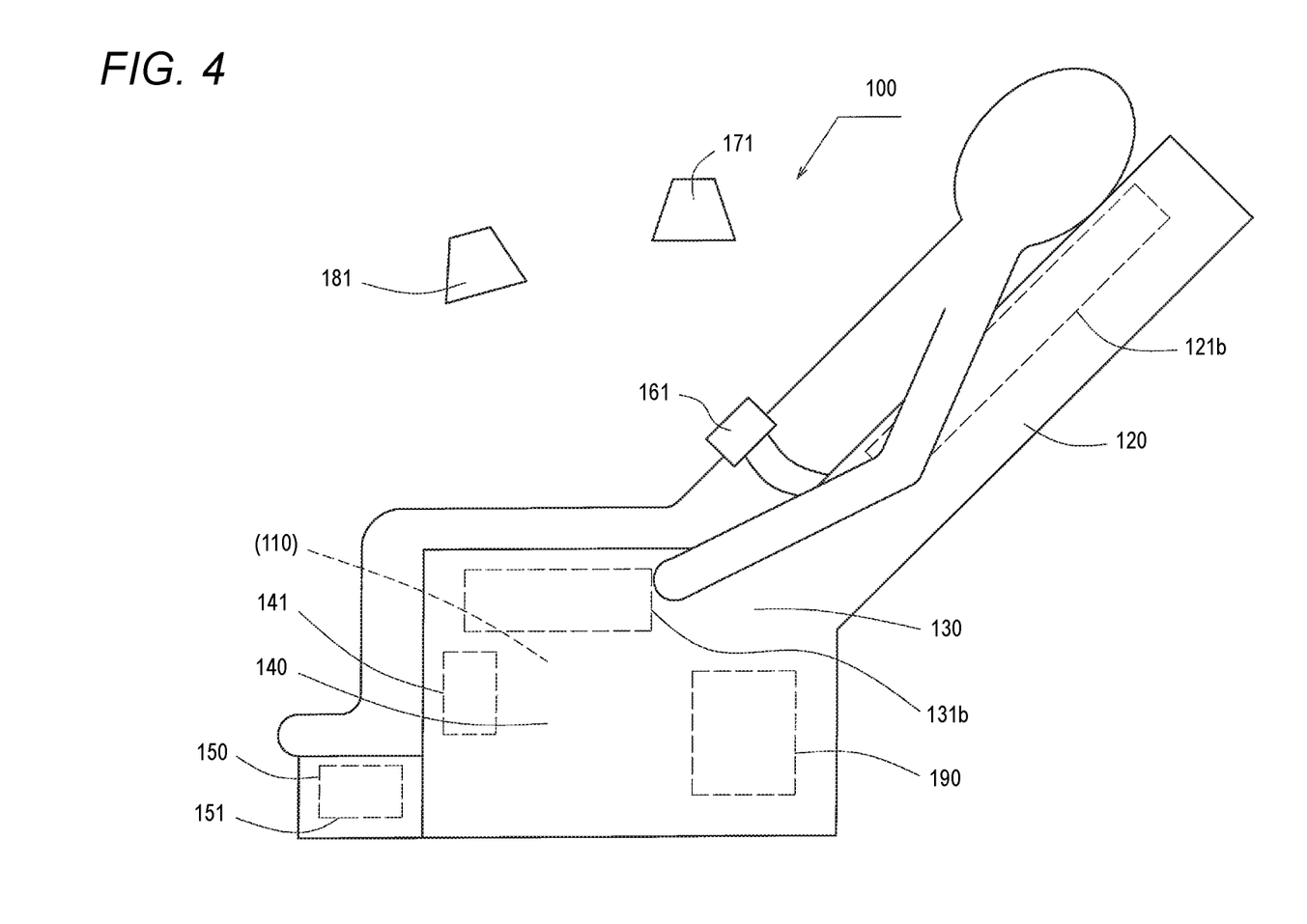
FIG. 4 is a side view showing a use state of the heating device according to the first embodiment.

FIG. 4 is a side view showing a use state of the heating device 100 according to the first embodiment. As shown in FIG. 4, the heating device 100 operates while the person is sitting on the seat portion 110.

In the heating device 100, as described above, the back heating units 121a, 121b heat the back of the person, the thigh side heating units 131a, 131b heat the outer side surfaces of the thigh portions of the person, and the calf heating units 141a, 141b heat the calves of the person.

The heating device 100 applies the person with the heating by any one or more of the temperature change units H1 and the stimulus by any one or more of the induction units C1. The induction area where the induction unit C1 applies the stimulus to the person is in the vicinity of the temperature change area heated by the temperature change unit H1. Details will be described later.

The back heating units 121a, 121b, the thigh side heating units 131a, 131b, and the calf heating units 141a, 141b heat respective portions of the person in a form of pulses. The temperature change unit H1 changes the temperature with an absolute value of a temperature change speed of the temperature change area within a range of 0.1° C./sec to 10° C./sec. The controller 190 performs the first control in which the absolute value of the temperature change speed of the temperature change area is within the range of 0.1° C./sec to 10° C./sec. Preferably, the absolute value is within a range of 0.2° C./sec to 9.9° C./sec.

As described above, the heating device 100 changes the temperature of the skin of a body surface in small increments.

4. Heating Pattern

Figure 5:
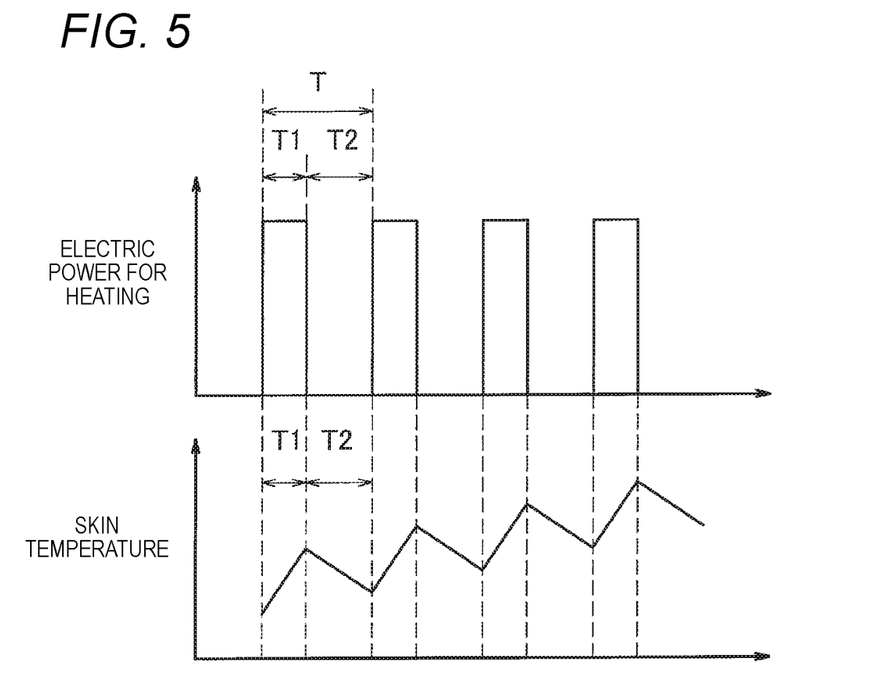
FIG. 5 is a graph showing a heating pattern of the heating device according to the first embodiment.

FIG. 5 is a graph showing a heating pattern of the heating device 100 according to the first embodiment. A horizontal axis in FIG. 5 indicates time. A vertical axis on an upper side in FIG. 5 indicates electric power for heating. A vertical axis on a lower side in FIG. 5 indicates the skin temperature.

For the sake of explanation, the calf heating units 141a, 141b will be described as an example. As shown in FIG. 5, the calf heating units 141a, 141b heat the calves of the person in the form of pulses. The temperature change unit H1 is a heating unit that increases the temperature of the temperature change area. The first control is a control for increasing the temperature of the temperature change area.

As shown in FIG. 5, the temperature change unit H1 increases the temperature of the temperature change area during a heating period T1, and lowers the temperature of the temperature change area during a non-heating period T2. That is, during the non-heating period T2, the skin is cooled. As a whole, an average temperature of the skin gently rises.

As shown in FIG. 5, the non-heating period T2 is longer than the heating period T1.

In FIG. 5, during the heating period T1, the skin temperature rises rapidly, and during the non-heating period T2, the skin temperature falls relatively slowly. An absolute value of a temperature change rate of the temperature change area in the non-heating period T2 is smaller than the absolute value of the temperature change rate of the temperature change area in the heating period T1.

The back heating units 121a, 121b and the thigh side heating units 131a, 131b heat respective portions of the person with the heating pattern in FIG. 5. As described above, the temperature change unit H1 of the heating device 100 heats the temperature change area while alternately repeating the heating period T1 during which the temperature change area is heated and the non-heating period T2 during which the temperature change area is not heated. That is, the temperature change unit H1 heats respective portions of the person in the form of pulses.

5. Thermal Referral

While the temperature change unit H1 changes the temperature of the temperature change area by the heating pattern as shown in FIG. 5, and in accordance therewith, the induction unit C applies at least one of the vibration and the light irradiation to the induction area. At this time, even though the induction area is not heated specially, the person feels the temperature on the induction area equal to or higher than the actual local skin temperature.

Thermal referral is applied to the heating device 100 according to the first embodiment. The thermal referral is an illusion phenomenon in which a person feels the temperature of the induction area equal to or higher than the actual skin temperature in a case where a temperature stimulus is applied to the temperature change area on the skin and a stimulus such as a tactile sensation is applied to the induction area.

6. Dermatomes (Relationship Between Temperature Change Area and Induction Area)

The skin can be classified into multiple dermatomes. One dermatome is thought to be an area controlled by a sensory nerve extending from one spinal nerve root.

Therefore, when a dermatome including the temperature change area and a dermatome including the induction area are close to each other, the effect of the thermal referral is easily obtained. For example, the dermatome including the temperature change area and the dermatome including the induction area are preferably the same or adjacent to each other.

Several dermatomes have been proposed. The present disclosure adopts a dermatomes in Keegan J J. and Garrett F D.: The segmental distribution of the cutaneous nerves in the limbs of man. Anat Rec 102 pp 409-437 (1948). However, some modifications are added as will be described later.

Figure 6:
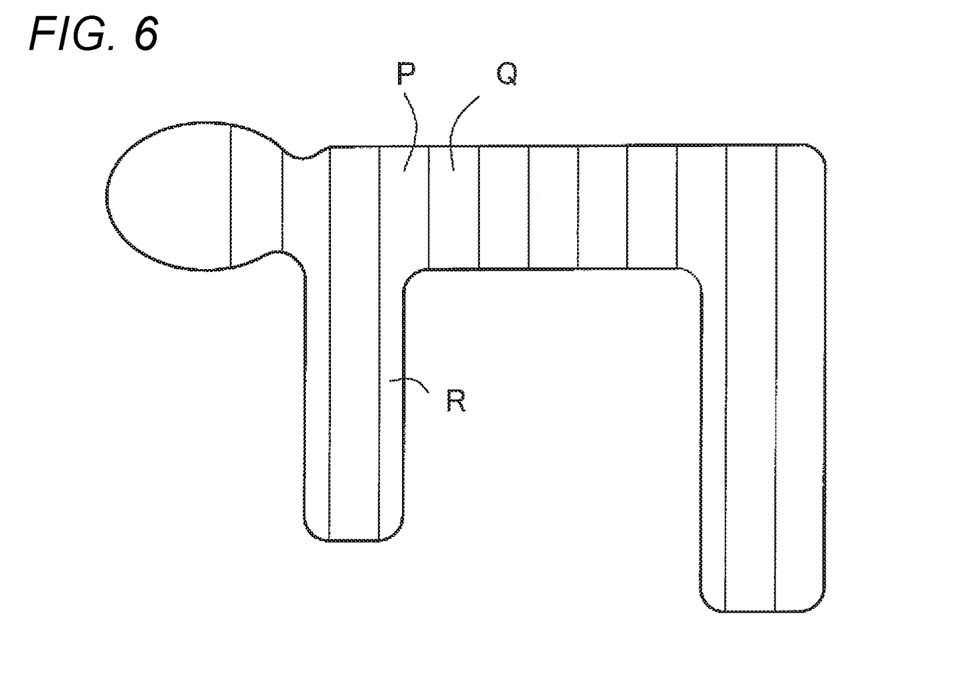
FIG. 6 is an example of a schematic view for explaining a dermatomes.

FIG. 6 is a simplified schematic diagram for explaining the dermatomes. As described above, the several dermatomes have been proposed and are not necessarily unique. FIG. 6 is a very simplified view for easy understanding of a concept of a dermatome common to those dermatomes.

As shown in FIG. 6, one dermatome occupies a band-shaped area depending on the height of the spinal nerve. As shown in FIG. 6, a dermatome including a point P and a dermatome including a point Q are adjacent to each other. The dermatome including the point P and a dermatome including a point R are the same.

A distance between the point P and the point Q is shorter than a distance between the point P and the point R. However, the dermatome including the point P and the dermatome including the point R is the same, whereas the dermatome including the point P and the dermatomes including the point Q are adjacent to each other. In this case, in a case where the point P is set as the temperature change area, if the point R is set to the induction area rather than the point Q, a high thermal referral effect can be obtained.

As described above, from FIG. 6, compared with a state where the temperature change area and the induction area are closer to each other in different dermatomes, even if a linear distance between the temperature change area and the induction area is longer, a state where the temperature change area and the induction are disposed in the same dermatome is preferable.

In the general definition of a dermatome, there is no distinction between left and right half bodies sandwiching a midline. However, the actual sensory nerves are divided into the left and right halves and integrated. Therefore, the dermatome in the present disclosure is defined to be different between a left half body and a right half body. The dermatome positioned on the right half body and the dermatome positioned on the left half body belong to different dermatomes. The term "dermatome" in the present disclosure is based on Keegan J J. and Garrett F D.: The segmental distribution of the cutaneous nerves in the limbs of man. Anat Rec 102 pp 409-437 (1948), and the dermatome is adopted that treats the dermatome on the left half body and the dermatomes on the right half body as different segments.

7. Effects of First Embodiment

The temperature change unit H1 of the heating device 100 heats the human skin surface by repeating the heating period T1 and the non-heating period T2. As described above, the human skin surface is changed in temperature in the small increments. Therefore, a temperature rise speed of the skin during the heating period T1 can be sufficiently increased. As described above, when the temperature rise speed of the skin is large, the person can easily feel warmth, and therefore the thermal referral easily occurs. That is, even in the unheated induction area, the person relatively strongly has a warmer feeling.

In the heating device 100, the person has a combination warm feeling of (1) the warm feeling due to the heating and (2) the warm feeling due to the thermal referral. The heating device 100 can make the person strongly feel the temperature on the induction area equal to or higher than the actual temperature by redistributing or emphasizing the warm feeling felt at a heated site. The heating device 100 may only locally heat a portion of the human skin without heating the air over the entire volume indoors or in an automobile.

Therefore, the heating device 100 can make the person feel warmer indoors or in the automobile at a stage in which a heating appliance is just turned on and the indoor interior or the interior of the automobile is not warmed up much. That is, comfort of the person is improved.

The heating device 100 actually heats only a portion of the human skin. Therefore, each heating unit may be small. In addition, an amount of the heat output by the heating device 100 may be small. As a result, power consumption of the heating appliance such as a heater or an air conditioner can be reduced, and an energy-saving effect can be expected.

The non-heating period T2 is longer than the heating period T1. In the non-heating period T2, since the skin is naturally cooled, the skin temperature rises rapidly during the heating period T1, and the skin temperature falls relatively slowly during the non-heating period T2. Since the non-heating period T2 is longer than the heating period T1, the overall skin temperature can be raised gently. That is, excessive heating of the skin can be avoided.

8. Modification 8-1. Temperature Change Unit

The heating device 100 may include a foot sole heating unit that heats the foot soles of the person. The foot sole heating unit may heat the right foot and the left foot of the person, respectively. The foot sole heating unit may be integrated with the foot sole vibration unit 151. In addition, the heating device 100 may also heat other portions.

Other than the heating unit, any temperature change unit can be used as long as it changes the temperature of the human skin surface.

8-2. Vibration Unit

The heating device 100 may include a foot back vibration unit that vibrates a foot back (instep of a foot) of the person. In addition, the heating device 100 may also vibrate other portions. Further, the light may be irradiated instead of the vibration.

8-3. Stimulus Synchronization

The tactile stimulus applied to the induction area by the induction unit C1 may be synchronized with a cycle T in which the temperature change unit H1 heats the temperature change area. Similarly, the visual stimulus may be synchronized with the cycle T in which the temperature change unit H1 heats the temperature change area. This is because the person easily feels warmth in the induction area.

8-4. Stimulus Type

In the first embodiment, the tactile stimulus by the vibration and the visual stimulus by the light are used as types of stimulus to be presented to the person. However, a tactile stimulus and a visual stimulus different from those in the first embodiment may be used. For example, in the case of applying the visual stimulus, luminance may be reduced.

8-5. Animal

The dermatomes are present in an animal as well. Therefore, the heating device 100 according to the present embodiment can also give the animal the warm feeling. Accordingly, the temperature change area and the induction area are areas on human or animal skin surface.

8-6. Induction Area

The induction area may not necessarily be an area on the human or animal skin surface. For example, even when the light is applied to a surface of clothing of the person, the effect of the first embodiment can be obtained as long as the person can visually recognize an irradiated portion. That is, the induction area may be an area that occupies a space that can be perspectival projected on the human or animal skin surface from a viewpoint of the person or animal.

8-7. Bed Type

The heating device 100 has a chair-type shape, but the heating device 100 may also have a bed-type shape or other shapes. In this case, a portion where a bed-type heating device applies a stimulus such as the heating may be different from that of the first embodiment. In addition, the heating device 100 may be wearable. In this case, the heating device 100 may have a shape of the clothes, or may have a shape that can be worn on a body of the person such as an arm or a leg.

8-8. Combination

The above modifications may be freely combined.

Second Embodiment

A second embodiment will be described. The difference between the second embodiment and the first embodiment is that the temperature change unit changes the temperature at a plurality of portions on the skin surface in the second embodiment.

1. Heating Device

A mechanical configuration of the heating device 10) according to the second embodiment is substantially the same as the mechanical configuration of the heating device 100 according to the first embodiment. The temperature change unit H1 has a second temperature change unit for changing a temperature of a second temperature change area of the temperature change area. That is, in the heating device 100, a first temperature change unit changes a temperature of a first temperature change area, and the second temperature change unit changes the temperature of the second temperature change area.

The second temperature change area is an area that does not overlap with the induction area. The controller 190 can execute a third control for changing the temperature of the second temperature change area. The third control is a second temperature change control.

2. Timing Chart

Figure 7:
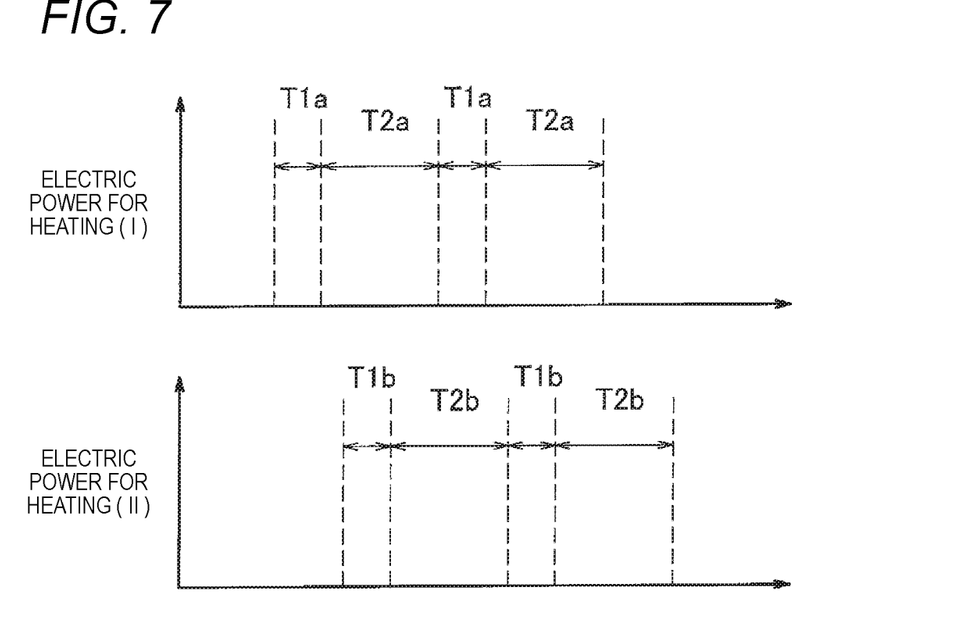
FIG. 7 is a graph showing a heating pattern of a heating device according to a second embodiment.

FIG. 7 is a graph showing a heating pattern of the heating device 100 according to the second embodiment. An upper diagram of FIG. 7 shows the first control in which the temperature change unit H1 changes the temperature of the first temperature change area. A lower diagram of FIG. 7 shows the third control in which the temperature change unit H1 changes the temperature of the second temperature change area. A horizontal axis in FIG. 7 indicates time.

As shown in FIG. 7, a heating period T1a during which the first temperature change area is heated and a non-heating period T2a during which the first temperature change area is not heated are alternately repeated. In addition, a heating period T1b during which the second temperature change area is heated and a non-heating period T2b during which the second temperature change area is not heated are alternately repeated. Further, the heating period T1a during which the first temperature change area is heated and the heating period T1b during which the second temperature change area is heated are different. That is, the timing of the first control is different from a timing of the third control.

In FIG. 7, the heating period T1a during which the first temperature change area is heated overlaps with the non-heating period T2b during which the second temperature change area is not heated. In addition, the heating period T1b during which the second temperature change area is heated overlaps with the non-heating period T2a in which the first temperature change area is not heated.

The second control is performed in accordance with the third control. A dermatome including the second temperature change area may be the same as or adjacent to the dermatome including the induction area. The dermatome including the second temperature change area may be the same as or adjacent to a dermatome including the first temperature change area.

3. Effects of Second Embodiment

The heating device 100 according to the second embodiment can apply the heating during the heating period T1a and the heating during the heating period T1b to the skin surface. Therefore, the warm feeling due to the thermal referral is easily maintained.

4. Modification 4-1. Plurality of Induction Units

As will be described later, the heating device 100 may include a second induction unit for applying a stimulus to a second induction area on the human skin surface.

4-2. Plurality of Temperature Change Units

The heating device 100 may include three or more temperature change units.

4-3. Combination

The second embodiment and the modification thereof may be freely combined with the first embodiment and the modification thereof.

Third Embodiment

A third embodiment will be described. The difference between the third embodiment and the first embodiment is that the induction unit applies the stimulus to the plurality of induction areas in the third embodiment.

1. Heating Device

The heating device 100 may include the second induction unit for applying the stimulus to the second induction area on the human skin surface. The second induction area is an area that does not overlap the temperature change area. The controller can execute a fourth control for applying a stimulus to the second induction area. The fourth control is performed in accordance with the first control. The fourth control is a second induction control.

2. Effects of Third Embodiment

By using the plurality of induction units in this manner, the warm feeling due to the thermal referral can be felt on the human skin surface with various spatio-temporal patterns.

The second induction area is preferably an area that does not overlap with the temperature change area.

3. Modification

The third embodiment may be freely combined with the first and second embodiments and the modifications thereof.

First to Third Embodiments

The controller 190 can execute the first control for changing the temperature of at least a part of the first temperature change area of the temperature change area, the second control for applying the stimulus to at least a part of the first induction area of the induction area, the third control for changing the temperature of the second temperature change area, and the fourth control for applying the stimulus to the second induction area (Experiment)

1. Experimental Method

While heating two portions of a left calf of a test subject, the heating unit is arranged on a right foot back, and the vibration unit is arranged in a left foot back. The left foot back is temperature-controlled to be constant at 32° C. The foot back is an instep portion of the foot. The two portions on the left calf are alternately heated in the form of pulses. The left foot back of the test subject is vibrated while the two portions on the left calf thereof are heated.

The test subject can operate an adjustment device for the heating unit of the right foot back. In a state where the left foot back of the test subject is vibrated while the two portions on the left calf thereof is heated, the test subject operates the adjustment device for the heating unit of the right foot back so as to feel the same warmth on the right foot back and the left foot back.

In this state, the temperatures of the two portions on the left calf and the left and right foot backs of the test subject are measured. The dermatome including the calf and the dermatome including the foot back are adjacent.

2. Experimental Results

Figure 8:
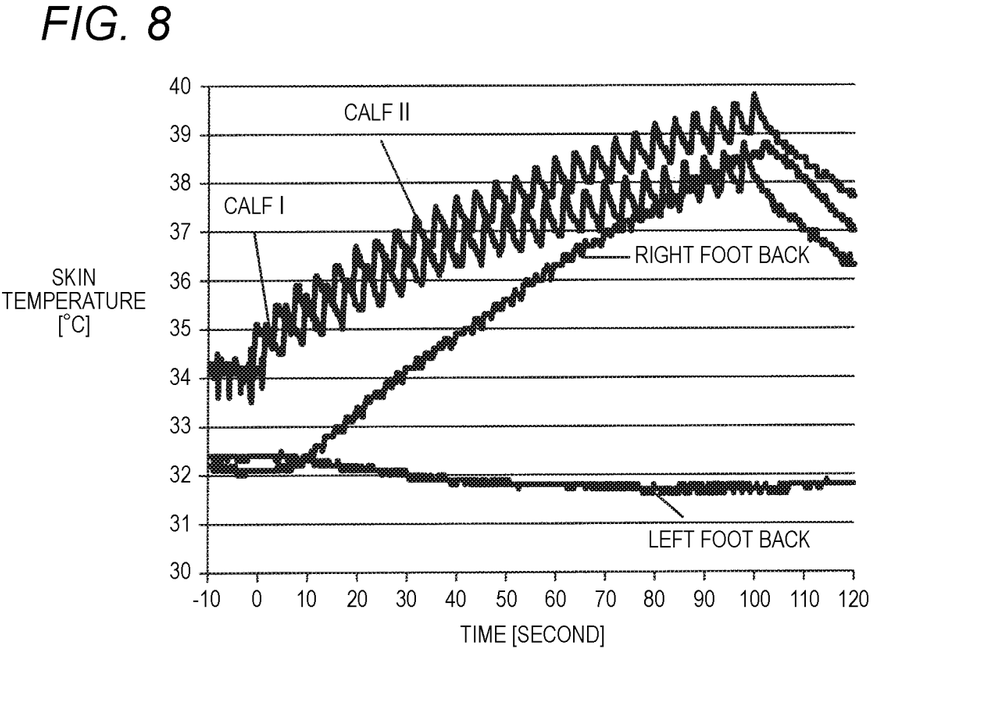
FIG. 8 is a graph showing experimental results of combination warm feeling.

FIG. 8 is a graph showing experimental results of combination warm feeling. A horizontal axis in FIG. 8 indicates time. A vertical axis in FIG. 8 indicates the skin temperature. As shown in FIG. 8, the skin temperature of the right foot back and the left calf gradually rises as a whole while repeating raising and lowering the skin temperature of the right foot back and the left foot back in the small increments. The temperature of the left foot back is kept at a constant value of about 32° C. The temperature of the right foot back rises due to the heating by the heating unit.

As shown in FIG. 8, after 100 seconds have elapsed from start of the experiment, the temperature of the left foot back is 32° C., and the temperatures of the right foot back and the left calf are about 38° C. to 39° C. The experiment is finished after 100 seconds have elapsed.

As described above, a temperature difference between the right foot back and the left foot is about 6° C. after 100 seconds elapse from the start of the experiment. However, the test subject has an illusion that the right foot back and the left foot back are at the same temperature. As described above, when the left calf is heated in the form of pulses, and the left foot back is vibrated, the test subject feels warmth on the left foot back even though the temperature of the left foot back does not rise.

3. Summary of Experiment

As described above, by using the heating unit and the vibration unit in combination, it is possible to make the test subject feel warmth on a vibration portion that is not a heating portion. Other tactile stimulus such as pressure can be used instead of the vibration unit. In addition, a visual stimulus such as applying light can also be used instead of the tactile stimulus. Further, the combination warm feeling lasts as long as 100 seconds.

(Appendix)

A heating device according to a first aspect including:
a temperature change unit for changing a temperature of a temperature change area on a human or animal skin surface:
an induction unit for applying a stimulus to an induction area and
a controller,
wherein the induction area is an area on the human or animal skin surface, or an area that occupies a space that can be perspectively projected on the human or animal skin surface from a viewpoint of a person or an animal,
wherein the induction area is an area that does not overlap with the temperature change area,
wherein the induction unit is configured to apply at least one of a tactile stimulus and a visual stimulus to the induction area,
wherein the controller is configured to execute a first control for changing a temperature of at least a part of a first temperature change area of the temperature change area and a second control for applying a stimulus to at least a part of a first induction area of the induction area, and
wherein the second control is performed in accordance with the first control.

The heating device according to a second aspect,
wherein the temperature change unit includes a second temperature change unit for changing a temperature of a second temperature change area of the temperature change area,
wherein the controller is configured to execute a third control for changing the temperature of the second temperature change area,
wherein a timing of the first control and a timing of the third control are different, and
wherein the second control is performed in accordance with the third control.

The heating device according to a third aspect,
wherein the induction unit includes a second induction unit for applying a stimulus to a second induction area of the induction area,
wherein the controller is configured to execute a fourth control for applying a stimulus to the second induction area, and
wherein the fourth control is performed in accordance with the first control.

The heating device according to a fourth aspect,
wherein a dermatomes including the temperature change area is close to a dermatomes including the induction area, and
wherein a dermatomes positioned on a right half body and a dermatomes positioned on a left half body belong to different dermatomes.

The heating device according to a fifth aspect,
wherein the dermatomes including the temperature change area is the same as or adjacent to the dermatomes including the induction area, and
wherein the dermatomes positioned on the right half body and the dermatomes positioned on the left half body belong to different dermatomes.

The heating device according to a sixth aspect,
wherein the temperature change unit sets an absolute value of a temperature change speed of the temperature change area within a range of 0.1° C./sec to 10° C./sec.

The heating device according to a seventh aspect,
wherein a start timing of the second control is a timing after a start timing of the first control and before an end timing of the first control.

The heating device according to an eighth aspect,
wherein the temperature change unit is a heating unit that increases the temperature of the temperature change area, and The first control is a control for increasing the temperature of the temperature change area.

The heating device according to a ninth aspect,
wherein pressure variation in a contact range before and after the temperature change in the temperature change area is less than a discrimination threshold of the person or animal.

The heating device may be applied to a seat. That is, the seat includes a heating device having a temperature change unit that is configured to change a temperature of a temperature change area on a human or animal skin surface, an induction unit that is configured to apply a stimulus to an induction area, and a controller. In the seat, the induction area is an area on the human or animal skin surface, or an area that occupies a space that can be perspectively projected on the human or animal skin surface from a viewpoint of a person or an animal, the induction area is an area that does not overlap with the temperature change area, the induction unit is configured to apply at least one of a tactile stimulus and a visual stimulus to the induction area, the controller is configured to execute a first control for changing a temperature of at least a part of a first temperature change area of the temperature change area and a second control for applying a stimulus to at least a part of a first induction area of the induction area, and the second control is performed in accordance with the first control.

What is claimed is:
1. A heating device comprising:
a heater that is configured to change a temperature of a temperature change area on a human or animal skin surface,
an inductor that is configured to apply a stimulus to an induction area; and
a controller,
wherein the induction area is an area on the human or animal skin surface, or an area that occupies a space that can be perspectively projected on the human or animal skin surface from a viewpoint of a person or an animal,
the induction area is an area that does not overlap with the temperature change area,
the inductor is configured to apply at least one of a tactile stimulus and a visual stimulus to the induction area, is separate from the heater, and does not apply heat to the induction area,
the controller is configured to execute a first control for changing a temperature of at least a part of a first temperature change area of the temperature change area and a second control for applying a stimulus to at least a part of a first induction area of the induction area, and
the second control is performed in accordance with the first control.
2. The heating device according to claim 1,
wherein the heater includes a second heater that is configured to change a temperature of a second temperature change area of the temperature change area,
the controller is configured to execute a third control for changing the temperature of the second temperature change area, a timing of the first control and a timing of the third control are different, and the second control is performed in accordance with the third control.

3. The heating device according to claim 1,
wherein the inductor includes a second inductor that is configured to apply a stimulus to a second induction area of the induction area, the controller is configured to execute a fourth control for applying a stimulus to the second induction area, and the fourth control is performed in accordance with the first control.

4. The heating device according to claim 1,
wherein a dermatome including the temperature change area is close to a dermatome including the induction area, and a dermatome positioned on a right half body and a dermatome positioned on a left half body belong to different dermatomes.

5. The heating device according to claim 1,
wherein a dermatome including the temperature change area is the same as or adjacent to a dermatome including the induction area, and a dermatome positioned on a right half body and a dermatome positioned on a left half body belong to different dermatomes.

6. The heating device according to claim 1,
wherein the heater sets an absolute value of a temperature change speed of the temperature change area within a range of 0.1° C./sec to 10° C./sec.

7. The heating device according to claim 1,
wherein a start timing of the second control is a timing after a start timing of the first control and before an end timing of the first control.

8. The heating device according to claim 1,
wherein the heater increases the temperature of the temperature change area, and the first control is a control for increasing the temperature of the temperature change area.

9. The heating device according to claim 1,
wherein pressure variation in a contact range before and after the temperature change in the temperature change area is less than a discrimination threshold of the person or animal.

10. A heating device comprising:
a heater that is configured to change a temperature of a temperature change area on a human or animal skin surface, an inductor that is configured to apply a stimulus to an induction area; and a controller, wherein the induction area is an area on the human or animal skin surface, or an area that occupies a space that can be perspectively projected on the human or animal skin surface from a viewpoint of a person or an animal, the induction area is an area that does not overlap with the temperature change area, the inductor is configured to apply at least one of a tactile stimulus and a visual stimulus to the induction area, the controller is configured to execute a first control for changing a temperature of at least a part of a first temperature change area of the temperature change area and a second control for applying a stimulus to at least a part of a first induction area of the induction area, the second control is performed in accordance with the first control, wherein the heater includes a second heater that is configured to change a temperature of a second temperature change area of the temperature change area, the controller is configured to execute a third control for changing the temperature of the second temperature change area, a timing of the first control and a timing of the third control are different, and the second control is performed in accordance with the third control.

11. A heating device comprising:
a heater that is configured to change a temperature of a temperature change area on a human or animal skin surface, an inductor that is configured to apply a stimulus to an induction area; and a controller, wherein the induction area is an area on the human or animal skin surface, or an area that occupies a space that can be perspectively projected on the human or animal skin surface from a viewpoint of a person or an animal, the induction area is an area that does not overlap with the temperature change area, the inductor is configured to apply at least one of a tactile stimulus and a visual stimulus to the induction area, the controller is configured to execute a first control for changing a temperature of at least a part of a first temperature change area of the temperature change area and a second control for applying a stimulus to at least a part of a first induction area of the induction area, the second control is performed in accordance with the first control, wherein the inductor includes a second inductor that is configured to apply a stimulus to a second induction area of the induction area, the controller is configured to execute a fourth control for applying a stimulus to the second induction area, and the fourth control is performed in accordance with the first control.

12. A heating device comprising:
a heater that is configured to change a temperature of a temperature change area on a human or animal skin surface, an inductor that is configured to apply a stimulus to an induction area; and a controller, wherein the induction area is an area on the human or animal skin surface, or an area that occupies a space that can be perspectively projected on the human or animal skin surface from a viewpoint of a person or an animal, the induction area is an area that does not overlap with the temperature change area, the inductor is configured to apply at least one of a tactile stimulus and a visual stimulus to the induction area, the controller is configured to execute a first control for changing a temperature of at least a part of a first temperature change area of the temperature change area and a second control for applying a stimulus to at least a part of a first induction area of the induction area, and the second control is performed in accordance with the first control, wherein pressure variation in a contact range before and after the temperature change in the temperature change area is less than a discrimination threshold of the person or animal.

* * * * *